United States Patent [19]

Mougin

[11] Patent Number: 6,126,929

[45] Date of Patent: Oct. 3, 2000

[54] COSMETIC COMPOSITION COMPRISING A MIXTURE OF POLYMER PARTICLES CAPABLE OF BEING FILM-FORMED AND PARTICLES NOT CAPABLE OF BEING FILM-FORMED

[75] Inventor: Nathalie Mougin, Paris, France

[73] Assignee: L'Oreal S.A., Paris, France

[21] Appl. No.: 09/142,939

[22] PCT Filed: Jan. 16, 1998

[86] PCT No.: PCT/FR98/00080

§ 371 Date: Oct. 21, 1998

§ 102(e) Date: Oct. 21, 1998

[87] PCT Pub. No.: WO98/31329

PCT Pub. Date: Jul. 23, 1998

[30] Foreign Application Priority Data

Jan. 20, 1997 [FR] France ................... 97 00545

[51] Int. Cl.[7] .............. A61K 31/74; A61K 9/50
[52] U.S. Cl. .............. 424/70.7; 424/78.03; 424/501
[58] Field of Search .............. 424/70.7, 78.03, 424/501

[56] References Cited

U.S. PATENT DOCUMENTS 5,925,337  7/1999  Arraudeau et al. ............ 424/70.7

FOREIGN PATENT DOCUMENTS

| | | |
|---|---|---|
| 0 288 012 | 10/1988 | European Pat. Off. . |
| 0 764 436 | 3/1997 | European Pat. Off. . |
| 2 528 699 | 6/1983 | France . |
| 2 238 242 | 5/1991 | United Kingdom . |
| WO 91/12793 | 9/1991 | WIPO . |

OTHER PUBLICATIONS

Nicole Alberola et al., "Composites particulaires : modélisation du comportement viscoélastique, assortie du concept de percolation", C.R. Acad. Sci. Paris, t. 319, Série II, pp. 1129–1134, 1994.

English Language Derwent Abstract of EP 0 764 436.

English Language Derwent Abstract of FR 2 528 699.

*Primary Examiner*—Carlos A. Azpuru
*Attorney, Agent, or Firm*—Finnegan, Henderson, Farabow, Garrett & Dunner, L.L.P.

[57] ABSTRACT

The present invention is directed to cosmetic or dermatological compositions comprising, in a cosmetically acceptable aqueous medium, as an agent for coating keratin fibres, from 15 to 60% by weight of solids of a film-forming mixture comprising:

(A) at least one aqueous dispersion of polymer particles which can form a film by themselves or can form a film in the presence of at least one plasticizer; the glass transition temperature Tg of the polymer or of the polymer/plasticizer mixture being less than or equal to 25° C.; and (B) at least one aqueous dispersion of spherical or anisotropic, non-film-forming particles capable of forming a percolation network in the matrix of the film formed from the film-forming particles and from the optional plasticizer; the said non-film-forming particles are different from the pigments and are present in the said film-forming mixture in concentrations ranging from 20 to 90% by volume when they are spherical and in concentrations ranging from 10 to 80% by volume when they are anisotropic. These compositions can be used as bases for make-up products for the eyelashes and the eyebrows, or as bases for hair products for styling and/or maintaining the hair.

48 Claims, No Drawings

COSMETIC COMPOSITION COMPRISING A MIXTURE OF POLYMER PARTICLES CAPABLE OF BEING FILM-FORMED AND PARTICLES NOT CAPABLE OF BEING FILM-FORMED

This application is a U.S. National Stage Application filed under 35 U.S.C. § 371 of International Application No. PCT/FR98/00080, filed Jan. 16, 1998, which claims foreign priority benefit of French Application No. 97/00545, filed Jan. 20, 1997.

The present invention relates to cosmetic or dermatological compositions comprising, in a cosmetically acceptable aqueous medium, as an agent for coating keratin fibres, a film-forming mixture consisting of particles of film-forming polymer and of rigid, non-film-forming particles, as well as to their use in the cosmetics or dermopharmacy field, in particular in products for making up the eyelashes and the eyebrows and in hair styling and/or hair maintenance products.

Two types of traditional mascara formulation are known, i.e. so-called "cream" aqueous mascaras in the form of an emulsion of wax in water, and so-called "waterproof" mascaras, which are anhydrous or have a low water content and which are dispersions of waxes in oils.

Conventional cream mascaras generally distribute themselves well along the eyelashes and form a uniform deposit along the eyelashes, and produce satisfactory lengthening of the eyelashes. However, they have the drawback of being relatively non-resistant to water and ambient moisture (rain, tears, baths, etc.) and have poor mechanical properties such as resistance to dry rubbing (passing the hand over the eyelids).

Conventional waterproof mascaras have very high resistance to water and to ambient moisture, but have poor properties as regards deposition and distribution of the product along the eyelashes, coloration of the eyelashes and as regards the mechanical properties, and, moreover, require the use of specific oil-based make-up-removing products on account of their high remanence to water.

In order to overcome these various technical problems, it has been proposed in recent years to add into traditional mascara formulations dispersions of film-forming polymer particles as agents which make it possible either to improve the water-resistance or to facilitate the removal of make-up or to improve the properties relating to making up the eyelashes. However, these wax-containing formulations lead to mechanical properties that are still insufficient.

One of the aims of the present invention is to make a new type of aqueous mascara formulation using, as an agent for coating the eyelashes, an aqueous dispersion of film-forming polymer particles optionally in the presence of a plasticizer, and which allows the drawbacks mentioned above to be solved.

The Applicant has observed that an aqueous mascara composition containing an aqueous suspension of pigments and using, as agent for coating the eyelashes, a suspension of film-forming polymer particles optionally in the presence of a plasticizer, leads to a heterogeneous, discontinuous, undesirable deposit on the eyelashes. The addition of surfactants to the mascara formulation in order to lower its surface tension to a value below that of the surface energy of an eyelash does not allow this phenomenon to be eliminated.

It is thus desirable to design novel mascara formulations based on film-forming polymer particles and pigments in suspension, which allow this phenomenon to be attenuated considerably or even eliminated altogether.

The hairstyling compositions of the prior art using, as main or auxiliary agent for coating the hair, an aqueous dispersion of film-forming polymer particles optionally in the presence of plasticizers, also have a tendency to lead, after application and drying, to heterogeneous and discontinuous coating of the hair.

Another subject of the present invention is to prepare hair formulations for styling and/or maintaining the hair, which contain, as main agent for coating the eyelashes, an aqueous dispersion of film-forming polymer particles optionally in the presence of a plasticizer, and which allows this phenomenon to be substantially attenuated or even eliminated altogether.

The Applicant has discovered, surprisingly, that by combining certain types of aqueous dispersion of film-forming polymer particles with certain non-film-forming particles in specific proportions which will be defined later in the description, aqueous mascara formulations can be prepared containing a composite film-forming material which makes it possible not only to solve all the problems specific to mascaras as listed above, but also to obtain homogeneous and continuous coating of the eyelashes.

The Applicant has also discovered that this specific combination leads to the formation of a novel composite material which constitutes an agent for coating hair, having both good cosmetic properties, in particular as regards the feel and the ease of disentangling, good film-forming properties and satisfactory mechanical properties for maintaining the hair, and which makes it possible to obtain better coating of the hair.

The cosmetic or dermatological compositions in accordance with the invention are characterized in that they contain, in a cosmetically acceptable aqueous medium, as agent for coating keratin fibres, from 15 to 60% by weight of solids of a film-forming mixture consisting of:

(A) at least one aqueous dispersion of polymer particles which can form a film by themselves or can form a film in the presence of at least one plasticizer; the glass transition temperature Tg of the polymer or of the polymer/plasticizer mixture being less than or equal to 25° C.; and (B) at least one aqueous dispersion of spherical or anisotropic, non-film-forming particles capable of forming a percolation network in the matrix of the film formed from the film-forming particles and from the optional plasticizer;

the said non-film-forming particles are different from the pigments and are present in the said film-forming mixture in concentrations ranging from 20 to 90% by volume when they are spherical and in concentrations ranging from 10 to 80% by volume when they are anisotropic.

The expression "percolation network in the matrix of the polymer which has formed a film" is understood to refer to the network formed by the non-film-forming particles by interconnection and formation of aggregates, dispersed inside all of the matrix of the polymer film at and above a certain volume-fraction threshold of the said particles in the film-forming mixture of the invention. Below this threshold, the non-film-forming particles are not percolating and are distributed randomly in the matrix of the polymer film. This type of behaviour is described in the article by Nicole Alberola, Corinne Bas and Patrice Mele, C. R. Sci. Paris, t. 319, 2nd series, pp. 1129–1134, 1994.

In order to obtain both rapid film formation, good adhesion to the keratin fibres, good mechanical strength, good resistance to dry-rubbing of the composite material applied to the keratin support after drying, without a sticky effect, the non-film-forming particles according to the invention must be present in the mixture consisting of the film-forming polymer particles and the non-film-forming particles in concentrations ranging from 20 to 90% by volume, and preferably from 20 to 80% by volume, when they are spherical, and in concentrations ranging from 10 to 80% by volume, and preferably from 10 to 70% by volume, when they are anisotropic.

When the volume-fraction of the non-film-forming particles in the film-forming mixture is below the minimum volume-fractions indicated above, the percolation network in the matrix of polymer which has formed a film no longer forms and the mechanical properties of the coating on the keratin fibres are no longer satisfactory. A sticky deposit is also obtained on the fibre after drying in this case. When the volume-fraction of the non-film-forming particles in the film-forming mixture is above the maximum volume-fractions indicated above, poor film formation of the composite material on the fibre is observed.

The film-forming polymer particles are chosen from all the known types of polymers in cosmetics which are capable of forming, in the presence or absence of plasticizers, a film-forming material having a glass transition temperature Tg of less than or equal to 25° C. and more preferably ranging from −50° C. to 25° C.

In order to obtain faster film formation and better adhesion of the composite material resulting from the combination of the invention to the keratin support (eyelash, eyebrow or hair), the glass transition temperature Tg of the polymer or of the polymer/plasticizer mixture will preferably be less than or equal to 10° C.

Among the polymers constituting the film-forming particles, mention may be made, for example, of polymers containing ethylenic unsaturation, such as polyacrylics, polyvinyls, polyolefins; polycondensates such as polyurethanes, polyesters, polyamides, polyureas; natural polymers or modified natural polymers, such as certain cellulose ethers, for instance the product Aquacoat sold by SEPPIC (ethylcellulose pseudolatex) or certain cellulose esters, for instance the product CAB-SU 160 sold by Eastman (partially neutralized cellulose acetobutyrate succinate latex).

In order to obtain better removal with shampoo in the context of the hair compositions or better removal of make-up by conventional surfactant solutions in the context of make-up products for the eyelashes or the eyebrows, while at the same time retaining good remanence to water and to ambient moisture, it will be preferred to use amphoteric film-forming polymers containing monomers bearing amphoteric groups such as betaine monomers or anionic polymers containing monomers bearing ionized or ionizable anionic groups, in particular carboxylic acid groups and/or sulphonic acid groups and/or phosphoric acid groups. The proportion of amphoteric or anionic monomer will generally range from 2 to 15% by weight relative to the total weight of the monomers constituting the film-forming polymer.

The betaine or acid groups are preferably partially or totally neutralized, such that the final pH of the mixture consisting of the aqueous dispersion of film-forming particles and the aqueous dispersion of rigid, non-film-forming particles is between 4 and 8 and more preferably between 6 and 7.5.

The neutralizing agents are preferably chosen from inorganic bases such as sodium hydroxide or potassium hydroxide or amino alcohols taken, for example, from the group consisting of 2-amino-2-methyl-1-propanol (AMP), triethanolamine, triisopropanolamine (TIPA), monoethanolamine, tri[1-(2-hydroxy)propyl]amine, 2-amino-2-methyl-1,3-propanediol (AMPD) and 2-amino-2-hydroxymethyl-1,3-propanediol.

The molecular weight, measured by steric exclusion chromatography, of these film-forming polymers is generally less than or equal to 500,000.

The non-film-forming particles of the invention can be of any nature. They can be inorganic or organic, spherical or anisotropic (for example in the form of ellipsoids, discs, platelets, sticks or fibrils). They are different from the pigments usually used in cosmetic or dermatological compositions.

Throughout the description, the term "pigment" is understood to refer to any natural or synthetic substance (or materials) consisting of fine particles that are insoluble in their working medium, the main function of which consists in giving coloration or covering properties to keratin substances.

Among the colouring pigments, mention may be made, for example, of inorganic pigments such as zirconium oxide, cerium oxide, zinc oxide or chromium oxide, titanium dioxide and iron oxides, and organic pigments such as carbon black or D & C Red 36. Among the covering pigments, mention may be made of kaolin, talc, titanium oxide, zirconium oxide, barium sulphate and magnesium carbonate, or equivalents thereof.

When they are spherical, the average size of the non-film-forming particles of the invention is preferably less than or equal to 1 µm and more preferably less than or equal to 600 nm. When they are anisotropic, the largest size is preferably less than or equal to 30 µm and more preferably less than or equal to 10 µm.

The non-film-forming particles of organic type used according to the present invention are preferably particles of a polymer having a glass transition temperature T'g of greater than or equal to 50° C. and more particularly greater than 70° C.

Among the spherical inorganic non-film-forming particles which can be used, mention may be made, for example, of silicas. Among the anisotropic inorganic non-film-forming particles which can be used, mentioned may be made, for example, of clays (platelets) such as montmorillonites, laponites, bentonites, in particular the commercial product Optigel WA sold by Sud Chemie, inorganic microfibrils such as certain titanates, for instance the commercial product Fybex sold by DuPont de Nemours, and silicon carbide particles.

Among the spherical organic non-film-forming particles which can be used, mention will be made of:

polymers containing ethylenic unsaturation, such as polyacrylics or polyvinylics with a glass transition temperature of greater than or equal to 50° C.;

polycondensates such as polyurethanes or polyureas with a glass transition temperature of greater than or equal to 50° C.

The non-film-forming particles of the invention more preferably consist of spherical particles of crosslinked polymer.

Among the polymers constituting these particles, mention may be made, for example, of polymers or copolymers, which are preferably crosslinked, obtained by polymerization or copolymerization of a monomer or of a mixture of monomers chosen from the group consisting of linear, cyclic or branched $C_1$–$C_{10}$ alkyl acrylates or methacrylates such as methyl methylmethacrylate, tert-butyl methacrylate, cyclohexyl methacrylate, isobornyl acrylate or methacrylate; styrene; vinyltoluene; vinyl chloride, vinyl benzoate or vinyl tert-butylbenzoate; acrylic acid, methacrylic acid. The polymers which are particularly preferred are crosslinked copolymers of at least one linear, cyclic or branched $C_1$–$C_8$ alkyl methacrylate and of acrylic acid and/or of methacrylic acid.

The crosslinking agents are preferably chosen from those commonly used in radical polymerization. Mention may be made, for example, of diacrylates or dimethacrylates of ethylene glycol, of polyethylene glycol, of propylene glycol, of divinylbenzene or of pentaerythrityl di- or trimethacrylate; alkylenediol diacrylates or dimethacrylates, for instance hexanediol dimethacrylate. They are used in amounts preferably ranging from 0.1 to 50% by weight relative to the weight of the monomers constituting the non-film-forming polymer In order to obtain better removal with shampoo (aqueous solution of surfactants) in the context of the hair compositions, or better removal of make-up by standard solutions of surfactants in the context of make-up products for the eyelashes or the eyebrows, while at the same time retaining good remanence to water or to ambient moisture, it will also be possible to use non-film-forming particles consisting of amphoteric polymer containing monomers bearing amphoteric groups, such as betaine monomers, or non-film-forming particles consisting of anionic polymer containing monomers bearing ionized or ionizable anionic groups, in particular carboxylic acid groups and/or sulphonic acid groups and/or phosphoric acid groups. The proportion of amphoteric or anionic monomer will generally range from 2 to 15% by weight relative to the total weight of the monomers constituting the non-film-forming polymer.

The betaine or acid groups are preferably partially or totally neutralized, such that the final pH of the mixture consisting of the aqueous dispersion of film-forming particles and the aqueous dispersion of non-film-forming particles is between 4 and 8 and more preferably between 6 and 7.5.

Preferably, the mixture consisting of the film-forming particles and the rigid, non-film-forming particles is present, as solids, in the compositions of the invention in concentrations ranging from 25 to 60% by weight relative to the total weight of the composition.

The dispersions of film-forming or non-film-forming polymer particles according to the invention can be obtained by batchwise emulsion polymerization, according to a process comprising:

a) the preparation of a feedstock in the reactor containing water, optionally a buffer and an emulsifier;

b) addition of the monomers to the feedstock, at ambient temperature;

c) emulsification of the monomers;

d) heating to the polymerization temperature of the reaction medium in the presence of a radical initiator.

The process can also be performed in semi-continuous mode using a feedstock containing only the aqueous part, a small part of the monomer mixture and some of the initiator. The mixture is then heated to the reaction temperature and the remaining monomer mixture and the remaining initiator dissolved in an amount of water are both added simultaneously.

The compositions according to the invention can also optionally contain a plasticizer in order to improve the mechanical properties, the cosmetic properties and the adhesion to keratin fibres of the composite material deposited after application and drying.

Among the plasticizers which can be used according to the invention, mention may be made of:

the Carbitols from the company Union Carbide, i.e. Carbitol or diethylene glycol ethyl ether, methyl Carbitol or diethylene glycol methyl ether, butyl Carbitol or diethylene glycol butyl ether or hexyl Carbitol or diethylene glycol hexyl ether, the Cellosolves from the company Union Carbide, i.e. Cellosolve or ethylene glycol ethyl ether, butyl Cellosolve or ethylene glycol butyl ether, or hexyl Cellosolve or ethylene glycol hexyl ether, propylene glycol derivatives and in particular propylene glycol phenyl ether, propylene glycol diacetate, dipropylene glycol butyl ether and tripropylene glycol butyl ether, as well as the Dowanols from the company Dow Chemical, i.e. Dowanol PM or propylene glycol methyl ether, Dowanol DPM or dipropylene glycol methyl ether and Dowanol TPM or tripropylene glycol methyl ether.

Mention may also be made of:

diethylene glycol methyl ether or Dowanol DM from the company Dow Chemical, castor oil oxyethylenated with 40 mol of ethylene oxide, such as the product sold by the company Rhône-Poulenc under the name "Mulgofen LE-719", benzyl alcohol, triethyl citrate sold by the company Pfizer under the name "Citroflex-2", 1,3-butylene glycol.

diethyl, dibutyl and diisopropyl phthalates and adipates, diethyl and dibutyl tartrates, diethyl, dibutyl and 2-diethylhexyl phosphates, and glycerol esters such as glyceryl diacetate (diacetin) and glyceryl triacetate (triacetin).

The plasticizer is present in a proportion preferably ranging from 0 to 20% by weight relative to the weight of the mixture consisting of the film-forming polymer particles and the non-film-forming particles. This proportion varies depending on the intended application.

The cosmetically acceptable aqueous medium for the compositions of the invention preferably consists of water or a mixture of water and at least one solvent which is cosmetically acceptable and compatible with the non-film-forming particles and the film-forming particles, such as a monoalcohol, a polyalcohol, a glycol ether, acetone or an ester, alone or in the form of a mixture. It consists more particularly of water or of water and a $C_1$–$C_4$ lower alcohol, for instance ethanol or isopropanol.

The compositions according to the invention as defined above can be used as a base for a hair product for shaping and/or maintaining the hair style, in particular aerosol lacquers or pump-dispenser bottles for fixing the hair, hairsetting or blow-drying lotions and styling mousses or gels.

The hair compositions in accordance with the invention can also contain conventional cosmetic additives such as preserving agents, softeners, sequestering agents, fragrances, dyes, viscosity modifiers, propellants, pearlescent agents, moisturizers, antidandruff agents, antiseborrhoeic agents, sunscreens, hair conditioners, antioxidants, proteins and vitamins.

The compositions according to the present invention can be used as a base for a make-up product for the eyelashes and the eyebrows, such as a mascara or an eyeliner.

The make-up compositions for the eyelashes and the eyebrows generally contain pigments. These pigments can be organic or inorganic or can also be pearlescent pigments. Such pigments are well known and are described in particular in FR 83/09997 (2,528,699). They can be in the form of a pigmentary paste, for instance the commercial products Cosmenyl sold by the company Hoechst.

The make-up compositions for the eyelashes and the eyebrows according to the invention can also comprise at least one conventional additive chosen from a softener, a preserving agent, a sequestering agent, a fragrance, a thickener, an oil, a silicone, a cohesion agent, a basifying or acidifying agent, a filler, anionic surfactants and/or nonionic surfactants.

Another object of the invention consists in using the film-forming mixture consisting of:

the aqueous dispersion of film-forming polymer particles as defined above;

the aqueous dispersion of rigid, non-film-forming particles as defined above; as an agent for coating keratin fibres in and for the preparation of a cosmetic or dermatological composition.

Another object of the invention consists in using the said film-forming mixture in and for the preparation of a cosmetic or dermatological composition intended to be applied to keratin fibres and to form a homogeneous and continuous coating on the said fibres.

The examples which follow serve to illustrate the invention without, however, being limiting in nature.

EXAMPLE 1:

Preparation of a dispersion of rigid, non-film-forming acrylic polymer particles Composition of the polymer:

| methyl methacrylate | 91% by weight |
|---|---|
| methacrylic acid | 5% by weight |
| ethylene glycol dimethacrylate (crosslinking agent) | 4% by weight |

Procedure:

100 g of deionized water, 16 g of active material of an alkyl ethoxy sulphate surfactant sold under the name Abex JKB by the company Rhône-Poulenc and 2.5 g of potassium persulphate are introduced into a reactor equipped with a central mechanical stirrer, a thermometer and a condenser. The mixture is brought to a temperature of 80° C. with rapid stirring.

In parallel, the following two so-called "addition solutions" $S_1$ and $S_2$ are prepared:

Addition solution $S_1$ (monomer solution):

| Methyl methacrylate | 1820 g |
|---|---|
| Methacrylic acid | 100 g |
| Ethylene glycol dimethacrylate (crosslinking agent) | 80 g |

Addition solution $S_2$:

| Deionized water | 5000 g |
|---|---|
| Abex JKB | 160 g |
| Potassium persulphate | 7.5 g |

When the aqueous solution in the reactor has reached 80° C., 10% of the solution $S_1$ is added and the mixture is left to react for 15 minutes. The remainder of the solution $S_1$ and the solution $S_2$ are then added simultaneously over a period of 4 hours, at a constant flow rate. At the end of the two simultaneous additions, the temperature of the reaction medium is raised to 85° C. and this temperature is maintained for 30 minutes. The mixture is cooled to room temperature with stirring. It is filtered through a Nylon gauze.

A dispersion of polymer particles having the characteristics below is obtained:

Average particle size: 92 nm

Particle size polydispersity, measured by quasi-elastic light scattering with a machine such as a Coulter N4 SD:<0.1

Solids content in a ventilated oven at 80° C. to constant weight: 26.6%

EXAMPLE 2

Preparation of a dispersion of film-forming acrylic polymer particles

Composition of the polymer:

| Acrylic acid | 10% |
|---|---|
| Isobutyl acrylate | 70% |
| t-Butyl acrylate | 20% |

62.5 g of deionized water, 1.24 g of an aqueous 30.4% solution of alkyl ethoxysulphate surfactant sold under the name Abex JKB by the company Rhône-Poulenc and 0.19 g of potassium persulphate are introduced into a reactor equipped with a central mechanical stirrer, a thermometer and a condenser. The mixture is brought to a temperature of 80° C. with rapid stirring.

In parallel, the two so-called "addition solutions" $S_1$ and $S_2$ below are prepared:

Addition solution $S_1$ (monomer solution):

| Acrylic acid | 12.5 g |
|---|---|
| Isobutyl acrylate | 87.5 9 |
| t-Butyl acrylate | 25 g |
| Dodecanethiol | 1.25 g |

Addition solution $S_2$:

| Deionized water | 312.5 g |
|---|---|
| Abex JKB aqueous 30.24% solution | 11.16 g |
| Potassium persulphate | 0.55 g |

When the aqueous solution in the reactor has reached 80° C., 10 of the solution $S_1$ is added and the mixture is left to react for 15 minutes. The remainder of the solution $S_1$ and the solution $S_2$ are then added simultaneously over a period of 4 hours, at a constant flow rate. At the end of the two simultaneous additions, the temperature of the reaction medium is raised to 85° C. and this temperature is maintained for 30 minutes. The mixture is cooled to room temperature with stirring. It is filtered through a Nylon gauze.

A dispersion of polymer particles having the characteristics below is obtained:

Average particle size: 230 nm

Particle size polydispersity, measured by quasi-elastic light scattering with a machine such as a Coulter N4 SD:<0.1

Solids content in a ventilated oven at 80° C. to constant weight: 25%

Molecular weight at the peak height of steric exclusion chromatography: 70,000

Glass transition temperature measured by DSC:

EXAMPLE 3

Mascara

Composition A below is prepared:

| | |
|---|---|
| Dispersion of film-forming polymer particles of Example 2 (concentrated on a rotary evaporator to a solids content of 26.6%) | 50% by weight |
| Dispersion of non-film-forming polymer particles of Example 1 (26.6% solids) | 50% by weight |
| 2-Amino-2-methylpropanol qs | pH 7 |

Composition A obtained is concentrated on a rotary evaporator until a solids content of 40% by weight is obtained.

A mascara formulation is prepared by mixing the following ingredients, with magnetic stirring:

| | |
|---|---|
| Composition A | 93.3% by weight |
| Pigmentary paste sold under the name Cosmenyl black by Hoechst, containing 30% active material | 6.7% by weight |

Appearance of the coating with the mascara on hair fibres or on natural-coloured Polyamide fibres:

The appearance of the coating, with the mascara of the invention, of a natural-coloured polyamide fibre 100 μm in diameter (synthetic model of the eyelashes) or of a fibre obtained from blond Dutch hair (natural model of eyelashes) is then observed, the said polyamide fibres or hair fibres being prewashed with a standard make-up-removing solution such as the commercial product Effacil sold by the L'Oreal group, rinsed with osmosed water and then dried in the open air.

The mascara is applied to each type of fibre by three consecutive passages of the fibre through a small amount of mascara placed on a glass plate or in a plastic split conical applicator.

Irrespective of the nature of the fibre, a homogeneous, continuous coating of constant thickness (between 10 and 20 μm when dry) is obtained.

Water-resistance:

The water-resistance of the film obtained with the mascara is then evaluated by immersing the fibres, coated with mascara and then dried for 3 hours, in an amount of water which is sufficient to cover the said fibres. Without stirring, the films immersed swell slightly but do not become detached from the fibres thus treated.

Removal of make-up:

The aptitude to remove make-up of the mascara of the invention is also evaluated by immersing the fibres, coated with mascara and then dried for 24 hours, in an amount of a standard make-up-removing solution, such as the commercial product Effacil, which is sufficient to cover the said fibres. Gentle rubbing is carried out by passing a finger over the immersed film at different immersion times. The film becomes completely detached from the hair fibre after 1 min and from the polyamide fibre after 2 min.

EXAMPLE 4

Mascara

Composition B below is prepared:

| | |
|---|---|
| Dispersion of film-forming polymer particles of Example 2 (26.6% solids) | 30% by weight |
| Dispersion of non-film-forming polymer particles of Example 1 (26.6% solids) | 70% by weight |
| 2-Amino-2-methylpropanol qs | pH 8 |

Composition B obtained is concentrated on a rotary evaporator until a solids content of 40% by weight is obtained.

A mascara formulation is prepared by mixing together the ingredients below, with magnetic stirring:

| | |
|---|---|
| Composition B | 93.3% by weight |
| Pigmentary paste sold under the name Cosmenyl black by Hoechst, containing 30% active material | 6.7% by weight |

The same tests as those carried out for the mascara of Example 3 are performed. This mascara leads to homogeneous, continuous coating on a hair fibre or on a natural-coloured polyamide fibre. It has good water-resistance and is easily removed with a standard make-up remover (the film becomes completely detached from the hair fibre after 1 min and from the polyamide fibre after 2 min).

EXAMPLE 5

Mascara

A mascara formulation is prepared by mixing together the ingredients below, with magnetic stirring:

| | |
|---|---|
| Composition C | 50% by weight |
| Dispersion of non-film-forming polymer particles of Example 1 (40% solids) | 50% by weight |
| 2-Amino-2-methylpropanol qs | pH 7 |

The same tests as those carried out for the mascara of Example 5 are performed. This mascara leads to homogeneous, continuous coating on a hair fibre or on a natural-coloured polyamide fibre. It has good water-resistance and is easily removed with a standard make-up remover (the film becomes completely detached from the hair fibre after 1 min and from the polyamide fibre after 2 min).

EXAMPLE 6

Hairstyling product base

A hairstyling product base is prepared by mixing together the ingredients below, with magnetic stirring:

| | |
|---|---|
| Dispersion of non-film-forming anisotropic inorganic particles, sold under the name *Optigel WA by the company Sud Chimie (0.85% solids) | 20% by weight |
| Dispersion of film-forming polymer particles of Example 2 (40% solids) | 80% by weight |
| 2-Amino-2-methylpropanol qs | pH 8 |

*smectic bentonite in which the largest particle size is from 1 to 5 μm.

The appearance of the coating on fibres obtained from blond Dutch hair achieved by this composition under the same conditions used for the mascara of Example 3 is observed. This composition leads to homogeneous, continuous coating of a hair fibre.

The appearance of the coating by a composition containing only the dispersion of film-forming polymer of Example 2 is also observed. Such a composition leads to heterogeneous, discontinuous coating on a hair fibre.

EXAMPLE 7

Preparation of an aqueous dispersion of film-forming acrylic polymer particles Composition of the polymer (percentage by weight):

| | |
|---|---|
| Isobutyl acrylate | 97% |
| Acrylic acid | 3% |

50 g of deionized water, 0.3 g of Abex JKB surfactant and 0.154 g of potassium persulphate are introduced into a reactor equipped with a central mechanical stirrer, a condenser, a thermometer and a tube for bubbling nitrogen through. The mixture is brought to 80° C. with rapid stirring.

In parallel, the two so-called "addition solutions" $S_1$ and $S_2$ below are prepared:

Addition solution $S_1$ (monomer solution):

| | |
|---|---|
| Isobutyl acrylate | 97 g |
| Acrylic acid | 3 g |
| Dodecanethiol | 1 g |

Addition solution $S_2$:

| | |
|---|---|
| Deionized water | 250 g |
| Abex JKB (100% active material) | 2.7 g |
| Potassium persulphate | 0.446 g |

When the temperature of the feedstock has reached 80° C., 10% of the monomer mixture of the "addition solution No. 1" are added and the mixture is left to react for 15 minutes.

Simultaneous uniform addition over 4 hours of the remainder of the "addition solution No. 1" and of the "addition solution No. 21" is then commenced.

After these 4 hours of addition, the temperature is increased to 85° C. and these conditions are maintained for 30 minutes. The reaction medium is then allowed to cool to room temperature and is adjusted to pH 7 by addition of 2-amino-2-methylpropanol. The mixture is then filtered through Nylon gauze. The concentration of the latex is next brought from 25% to 40% solids by concentrating on a rotary evaporator.

Determination of the glass transition Tg=−20° C.

EXAMPLE 8

Preparation of an aqueous dispersion of film-forming acrylic polymer particles Composition of the polymer (percentage by weight):

| | |
|---|---|
| Isobutyl acrylate | 80% |
| Methyl methacrylate | 20% |

The polymer dispersion was prepared under the same conditions as those described in Example 8, without the step of adjusting the pH, using the "addition solutions" $S_1$ and $S_2$ below:

Addition solution $S_1$ (monomer solution):

| | |
|---|---|
| Isobutyl acrylate | 80 g |
| Methyl methacrylate | 20 g |
| Dodecanethiol | 1 g |

Addition solution $S_2$:

| | |
|---|---|
| Deionized water | 250 g |
| Abex JKB (100% active material) | 2.7 g |
| Potassium persulphate | 0.446 g |

A latex containing 40% solids was thus obtained.

Determination of the glass transition Tg=−3° C.

EXAMPLE 9

Mascara

The solids content of the dispersion of Example 1 was brought to 40° by concentration on a rotary evaporator.

A mixture of the three latices of Examples 1 (non-film-forming polymer particles), Example 8 and Example 9 (film-forming polymer particles) in the proportions below was then prepared:

| | |
|---|---|
| latex of Example 1 (40% solids) | 30 g |
| latex of Example 8 (40% solids) | 35 g |
| latex of Example 9 (40% solids) | 35 g |

The final pH of the mixture of the mixture was adjusted to 6.5 by addition of 2-amino-2-methyl-propanol. A mascara formulation was prepared by mixing this combination of three latices with the pigmentary paste Cosmenyl black from Hoechst, already used in Example 3, in the following proportions:

| mixture of the three latices | 93.3% by weight |
|---|---|
| pigmentary paste Cosmenyl black containing 30% active material | 6.7% by weight |

The coating properties imparted by this mascara were observed according to the conditions indicated in Example 3. Homogeneous, continuous coating of constant thickness was found.

What is claimed is:

1. A cosmetic or dermatological composition comprising, in a cosmetically acceptable aqueous medium, as an agent in said composition for coating keratin fibres, from 15 to 60% by weight of solids of at least one film-forming mixture comprising:
   (A) at least one aqueous dispersion of film-forming polymer particles, optionally including at least one plasticizer, wherein said film-forming polymer particles alone or said film-forming polymer particles combined with said optional at least one plasticizer have a glass transition temperature Tg no greater than 25° C.; and
   (B) at least one aqueous dispersion of spherical or anisotropic, non-film-forming particles in an amount effective to form a percolation network in the matrix formed from said at least one aqueous dispersion of film-forming polymer particles (A);
   wherein said non-film-forming particles are not pigments and are present in said at least one film-forming mixture in an amount ranging from 20 to 90% by volume when said non-film-forming particles are spherical and in an amount ranging from 10 to 80% by volume when said non-film-forming particles are anisotropic.

2. A cosmetic or dermatological composition according to claim 1, wherein said glass transition temperature Tg ranges from −50° C. to 25° C.

3. A cosmetic or dermatological composition according to claim 1, wherein said glass transition temperature Tg is no greater than 10° C.

4. A cosmetic or dermatological composition according to claim 1, wherein said film-forming polymer particles (A) are selected from polymers containing ethylenic unsaturation; polycondensates; natural polymers and modified natural polymers.

5. A cosmetic or dermatological composition according to claim 1, wherein said film-forming polymer particles (A) are selected from polyacrylics, polyvinylics, polyolefins, polyurethanes, polyesters, polyamides, polyureas, ethylcellulose pseudolatex, and partially neutralized cellulose acetobutyrate succinate latex.

6. A cosmetic or dermatological composition according to claim 1, wherein said film-forming polymer particles (A) are selected from amphoteric film-forming polymers containing monomeric residues bearing at least one amphoteric group and anionic polymers containing monomeric residues bearing at least one ionized or ionizable anionic group.

7. A cosmetic or dermatological composition according to claim 6, wherein said monomeric residues bearing at least one amphoteric group or said monomeric residues bearing at least one ionized or ionizable anionic group are present in an amount ranging from 2 to 15% by weight relative to the total weight of said monomeric residues constituting said film-forming polymer particles (A).

8. A cosmetic or dermatological composition according to claim 6, wherein said monomeric residues bearing at least one amphoteric group are betaine monomeric residues and said monomeric residues bearing at least one at least one ionized or ionizable anionic group are monomeric residues bearing at least one acid group selected from carboxylic acid groups, sulphonic acid groups and phosphoric acid groups.

9. A cosmetic or dermatological composition according to claim 8, wherein said betaine monomeric residues or said monomeric residues bearing at least one acid group are partially or totally neutralized and said at least one film-forming mixture has a pH ranging from 4 to 8.

10. A cosmetic or dermatological composition according to claim 9, wherein said pH ranges from 6 to 7.5.

11. A cosmetic or dermatological composition according to claim 1, wherein said film-forming polymer particles (A) have a molecular weight, measured by steric exclusion chromatography, of no greater than 500,000.

12. A cosmetic or dermatological composition according to claim 1, wherein said spherical non-film-forming particles (B) have an average size of no greater than 1 μm.

13. A cosmetic or dermatological composition according to claim 12, wherein said spherical non-film-forming particles (B) have an average size of no greater than 600 nm.

14. A cosmetic or dermatological composition according to claim 1, wherein said anisotropic non-film-forming particles (B) have a maximum size of no greater than 30 μm.

15. A cosmetic or dermatological composition according to claim 14, wherein said anisotropic non-film-forming particles (B) have a maximum size of no greater than 10 μm.

16. A cosmetic or dermatological composition according to claim 1, wherein said non-film-forming particles (B) are inorganic.

17. A cosmetic or dermatological composition according to claim 16, wherein said inorganic non-film-forming particles are selected from silicas, clays, titanate microfibrils and silicon carbides.

18. A cosmetic or dermatological composition according to claim 1, wherein said non-film-forming particles are organic.

19. A cosmetic or dermatological composition according to claim 18, wherein said organic non-film-forming particles have a glass transition temperature T'g of at least 50° C.

20. A cosmetic or dermatological composition according to claim 19, wherein said organic non-film-forming particles have a glass transition temperature T'g of greater than 70° C.

21. A cosmetic or dermatological composition according to claim 1, wherein said non-film-forming particles (B) are spherical particles of crosslinked polymer.

22. A cosmetic or dermatological composition according to claim 4, wherein said crosslinking agent that forms said crosslinked polymer is present in an amount ranging from 0.1 to 50% by weight relative to the weight of the monomeric residues comprising said non-film-forming polymer.

23. A cosmetic or dermatological composition according to claim 1, wherein said non-film-forming particles (B) are spherical particles of polymers selected from polymers containing ethylenic unsaturation and polycondensates.

24. A cosmetic or dermatological composition according to claim 23, wherein said polymers containing ethylenic unsaturation are selected from polyacrylics and polyvinylics and said polycondensates are selected from polyurethanes and polyureas.

25. A cosmetic or dermatological composition according to claim 1, wherein said non-film-forming particles (B) are selected from amphoteric non-film-forming polymers containing monomeric residues bearing at least one amphoteric group and anionic non-film-forming polymers containing monomeric residues bearing at least one ionized or ionizable anionic group.

26. A cosmetic or dermatological composition according to claim 25, wherein said monomeric residues bearing at least one amphoteric group or said monomeric residues bearing at least one ionized or ionizable anionic group is present in an amount ranging from 2 to 15% by weight relative to the total weight of monomeric residues constituting said non-film-forming polymer.

27. A cosmetic or dermatological composition according to claim 25, wherein said monomeric residues bearing at least one amphoteric group are betaine monomeric residues and said monomeric residues bearing at least one ionized or ionizable anionic group are monomeric residues bearing at least one acid group selected from carboxylic acid groups, sulphonic acid groups and phosphoric acid groups.

28. A cosmetic or dermatological composition according to claim 27, wherein said betaine monomeric residues or said monomeric residues bearing at least one acid group are partially or totally neutralized and said at least one film-forming mixture has a pH ranging from 4 to 8.

29. A cosmetic or dermatological composition according to claim 28, wherein said pH ranges from 6 to 7.5.

30. A cosmetic or dermatological composition according to claim 1, wherein said at least one film-forming mixture comprises at least one plasticizer in an amount of up to 20% by weight relative to the total weight of said at least one film-forming mixutre.

31. A cosmetic or dermatological composition according to claim 1, wherein said at least one film-forming mixture is present in an amount ranging from 25 to 60% by weight relative to the total weight of said cosmetic or dermatological composition.

32. A hair product for styling and/or maintaining hair comprising at least one cosmetic or dermatological composition according to claim 1.

33. A make-up product for eyelashes or eyebrows comprising at least one cosmetic or dermatological composition according to claim 1.

34. A make-up product according to claim 33, wherein said make-up product is mascara or eyeliner.

35. A method of homogenously and continuously coating keratin fibres comprising applying an effective amount of at least one cosmetic or dermatological composition according to claim 1 to said keratin fibres to homogenously and continuously coat said keratin fibres.

36. A method according to claim 35, wherein said keratin fibres are eyelashes.

37. A method according to claim 35, wherein said keratin fibres are hair.

38. A method of preparing a make-up product comprising including at least one cosmetic or dermatological composition according to claim 1 in said make-up product.

39. A method of preparing a hair product comprising including at least one cosmetic or dermatological composition according to claim 1 in said hair product.

40. A cosmetic or dermatological composition according to claim 1, wherein said cosmetically acceptable medium comprises water or water and at least one cosmetically acceptable solvent.

41. A cosmetic or dermatological composition according to claim 40, wherein said at least one cosmetically acceptable solvent is selected from monoalcohols, polyalcohols, glycol ethers, acetones and esters.

42. A cosmetic or dermatological composition according to claim 1, wherein said cosmetically acceptable medium comprises water or water and a C1–C4 lower alcohol.

43. A cosmetic or dermatological composition according to claim 42, wherein said C1–C4 lower alcohol is ethanol or isopropanol.

44. A hair product according to claim 32, wherein said hair product is in the form of an aerosol lacquer, a hairsetting lotion, a blow-drying lotion, a styling mousse, or a gel.

45. A hair product according to claim 32, wherein said hair product comprises at least one cosmetically acceptable additive.

46. A make-up product according to claim 33, wherein said make-up product further comprises at least one pigment.

47. A make-up product according to claim 46, wherein said make-up product further comprises at least one cosmetically acceptable additive.

48. A cosmetic or dermatological composition according to claim 1, wherein said at least one film-forming mixture in an amount ranging from 20 to 80% by volume when said non-film-forming particles are spherical and in an amount ranging from 10 to 70% by volume when said non-film-forming particles are anisotropic.

* * * * *

UNITED STATES PATENT AND TRADEMARK OFFICE
CERTIFICATE OF CORRECTION

PATENT NO. : 6,126,929
DATED : October 3, 2000
INVENTOR(S) : Nathalie Mougin

Page 1 of 1

It is certified that error appears in the above-identified patent and that said Letters Patent is hereby corrected as shown below:

<u>Claim 22, column 14,</u>
Line 52, change "claim 4" to -- claim 21 --.

Signed and Sealed this

Twenty-fifth Day of September, 2001

*Attest:*

*Attesting Officer*

NICHOLAS P. GODICI
*Acting Director of the United States Patent and Trademark Office*